United States Patent
Nam et al.

(10) Patent No.: US 7,795,501 B2
(45) Date of Patent: Sep. 14, 2010

(54) PROTEIN REGULATING LEAF LONGEVITY OF PLANTS, THE GENE THEREOF AND THEIR USE

(75) Inventors: Hong-gil Nam, Kyungbuk-do (KR); Jin-hee Kim, Busan (KR); Hye-ryun Woo, Kyungbuk-do (KR)

(73) Assignees: Genomine, Inc., Pohang, Kyungbuk (KR); Postech Foundation, Pohang, Kyungbuk (KR)

( * ) Notice: Subject to any disclaimer, the term of this patent is extended or adjusted under 35 U.S.C. 154(b) by 255 days.

(21) Appl. No.: 11/574,580

(22) PCT Filed: Aug. 31, 2005

(86) PCT No.: PCT/KR2005/002879

§ 371 (c)(1),
(2), (4) Date: Oct. 24, 2007

(87) PCT Pub. No.: WO2006/025693

PCT Pub. Date: Mar. 9, 2006

(65) Prior Publication Data

US 2008/0134354 A1    Jun. 5, 2008

(30) Foreign Application Priority Data

Sep. 1, 2004   (KR) .................. 10-2004-0069454

(51) Int. Cl.
C12N 15/82    (2006.01)
C12N 15/29    (2006.01)
C07K 14/415   (2006.01)
A01H 5/00     (2006.01)

(52) U.S. Cl. .............. 800/290; 530/370; 536/23.6; 435/320.1; 800/298

(58) Field of Classification Search ............ None
See application file for complete search history.

(56) References Cited

U.S. PATENT DOCUMENTS

2004/0031072 A1    2/2004   La Rosa et al.

FOREIGN PATENT DOCUMENTS

EP    2005781163    6/2007
WO    WO 02/050110  6/2002
WO    WO 03/018627  3/2003

OTHER PUBLICATIONS

Uniprot Accession No. Q9FYJ5, Mar. 1, 2001.*
GenBank Accession No. Q9FYJ5, Mar. 1, 2001.*
GenBank Accession No. AC000107, Aug. 9, 2000.*
Hamilton C.M. et al. Stable transfer of intact high molecular weight DNA into plant chromosomes. Proc Natl Acad Sci U S A. Sep. 3, 1996;93(18):9975-9.*
Whisstock J.C. et al. Prediction of protein function from protein sequence and structure. Q Rev Biophys. Aug. 2003;36(3):307-40. Review.*
WIPO, International Search Report for PCT/KR2005/002879.
EMBL database, Accession No. AC000107; website: http://www.ebi.ac.uk/cgi-bin/emblfetch?style=html&id=AC000107 &Submit=Go; cited in European Office Action dated Dec. 4, 2008 in corresponding European Application No. EP 2005781163.
Uniprot Database, Accession No. Q9FYJ5; website: http://www.uniprot.org/uniprot/Q9FYJ5; cited in European Office Action dated Dec. 4, 2008 in corresponding European Application No. EP 2005781163.
Article entitled "Identification of three genetic loci controlling leaf senescence in *Arabidopsis thaliana*" by Sung Aeong Oh et al., the Plant Journal (1997) Issue 12(3) pp. 527-535; cited in European Office Action dated Dec. 4, 2008 in corresponding European Application No. EP 2005781163.
Article entitled "Stress proteins on the yeast cell surface determine resistance to osmotin, a plant antifungal protein" Dae-Jin Yun et al., Plant Biology, Proc. Natl. Acad. Sci. USA 94 (1997) pp. 7082-7087; cited in European Office Action dated Dec. 4, 2008 in corresponding European Application No. EP 2005781163.

* cited by examiner

*Primary Examiner*—Cynthia Collins
(74) *Attorney, Agent, or Firm*—Intellectual Property Law Group LLP; Juneko Jackson; Otto O. Lee

(57) ABSTRACT

A novel protein, ORE 15, responsible for the regulation of plant leaf longevity is disclosed. Also, a gene encoding the protein ORE15 is disclosed. The protein and gene can be used in the regulation of plant leaf longevity, including delayed senescence, growth promotion, leaf weight, an size increase.

6 Claims, 4 Drawing Sheets

[Fig. 1]
[Fig. 2]
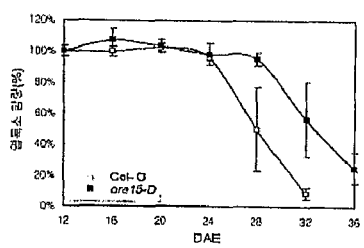
[Fig. 3]
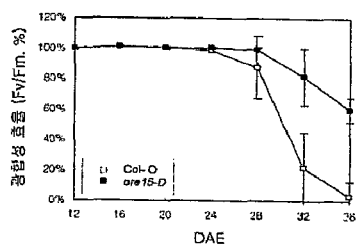
[Fig. 4]
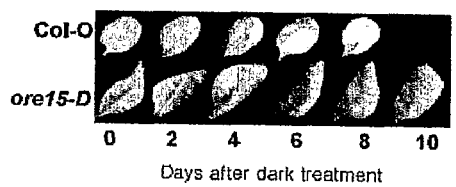
[Fig. 5]
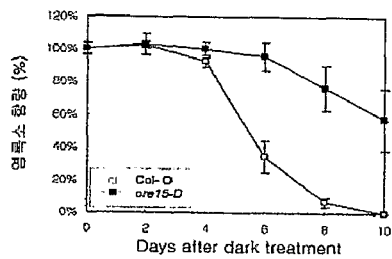

[Fig. 6]
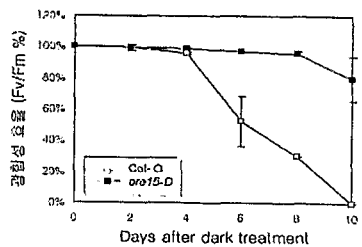
[Fig. 7]
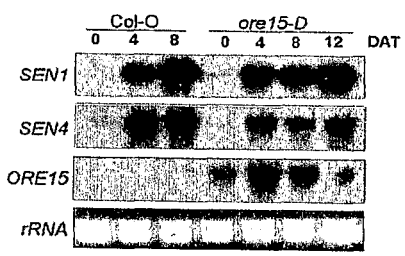
[Fig. 8]
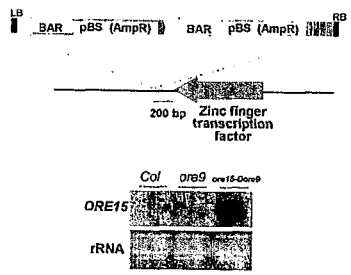
[Fig. 9]
```
MVREGEEEEE MMMMMATKPA WLEGLMASTF FSSCGIHETR RKSEKNVFCL  50
LCCLSVCPHC LPSHRSHPLL QVRRYVYHDV VRLSDLEKLI DCSYVQPYTI 100
NGARVIFLNQ RQQSRAKVSS NVCFTCDRIL QEPFHFCSLS CKVIILQQKF 150
GNYFTFRIDE SDPTFEGLRM DGHDQLGEIS TMEDGEDILV ISDESEQGNN 200
SHKKEKKKSK KKKPESNYLP MVLSSLGNRK GAPHRAPFS            239
```
[Fig. 10]
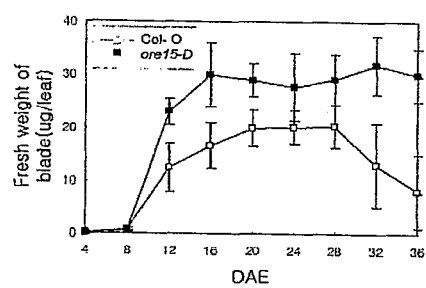

[Fig. 11]
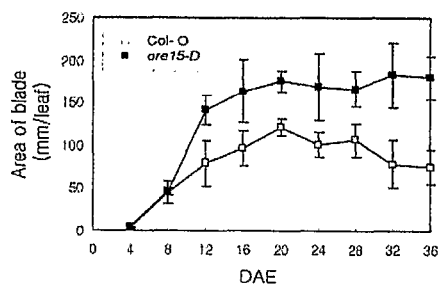
[Fig. 12]
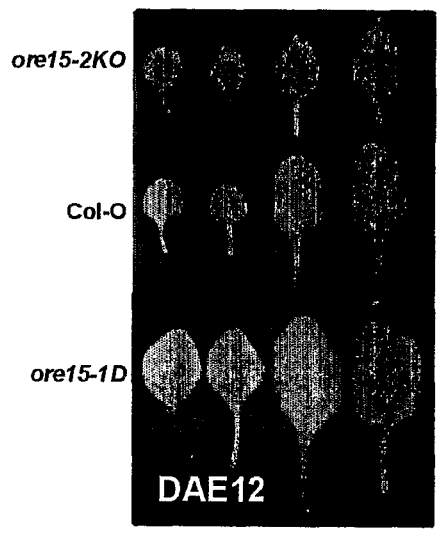
[Fig. 13]
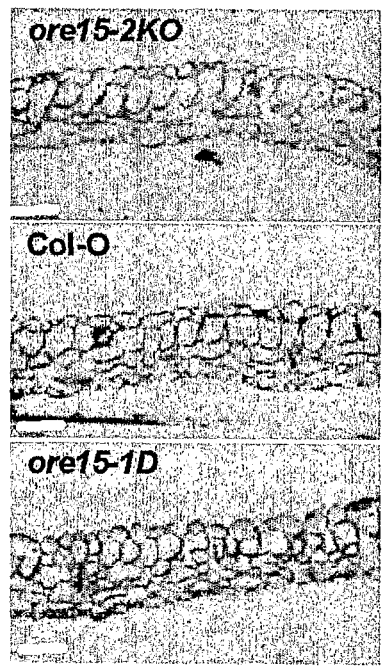

[Fig. 14]

|  | ore15-2KO | Col-0 | ore15-1D |
|---|---|---|---|
| Number of palisade cells aligned in: | | | |
| the leaf – width direction | 315.2(1.5) | 438.8(1.8) | 737.7(2.0) |
| the leaf – length direction | 141.2(1.6) | 175.8(1.1) | 286.8(2.9) |

SEQUENCE LISTING

```
<160> NUMBER OF SEQ ID NOS: 2

<210> SEQ ID NO 1
<211> LENGTH: 732
<212> TYPE: DNA
<213> ORGANISM: arabidopsis thaliana

<400> SEQUENCE: 1
atggttagag aaggtgaaga agaagaagag atgatgatga tgatggcaac gaaacctgca       60
tggcttgaag gtttaatggc ggagactttc ttctcaagct gtggaatcca cgaaactcgc      120
cgtaaaagtg aaaagaacgt tttttgctta ctctgttgtc tcagtgtttg tcctcactgt      180
ctcccttctc atcgctctca tcctcttctt caggtgagac gatacgtata ccacgacgtc      240
gttcggttga gtgatcttga gaagctcata gattgttcat atgttcagcc atatacaatt      300
aatggagcca aagtgatatt cttaaaccaa agacaacaat cacgagctaa ggtttcttca      360
```

-continued

```
aatgtttgct tcacttgtga tagaatcctt caagaaccat tccactttttg ttccctctct    420 tgcaaggtgg attatttatc atatcaagga gatgatttat caagcattct ctatagaatt    480
gatgaatcag attttacgtt cgagggtttg agaatggacg gacatgatca gctcggagag    540
atatcgacga tggaggatgg ggaggatata ctggtaattt cagatgaatc tgagcaaggt    600
aacaatagtc ataagaaaga gaagaagaag agcaagaaga agaagccaga gagcaattac    660
ttgcctggga tggttctttc atcacttggt aatagaagaa aaggtgctcc tcatagggct    720 ccttttttcat aa                                                        732
```

<210> SEQ ID NO 2
<211> LENGTH: 208
<212> TYPE: PRT
<213> ORGANISM: arabidopsis thaliana

<400> SEQUENCE: 2

```
Met Val Arg Glu Gly Glu Glu Glu Met Met Met Met Met Ala
  1               5                  10                  15

Thr Lys Pro Ala Trp Leu Glu Gly Leu Met Ala Glu Thr Phe Phe Ser
                 20                  25                  30

Ser Cys Gly Ile His Glu Thr Arg Arg Lys Ser Glu Lys Asn Val Phe
             35                  40                  45

Cys Leu Leu Cys Cys Leu Ser Val Cys Pro His Cys Leu Pro Ser His
     50                  55                  60

Arg Ser His Pro Leu Leu Gln Val Arg Arg Tyr Val Tyr His Asp Val
 65                  70                  75                  80

Val Arg Leu Ser Asp Leu Glu Lys Leu Ile Asp Cys Ser Tyr Val Gln
                 85                  90                  95

Pro Tyr Thr Ile Asn Gly Ala Lys Val Ile Phe Leu Asn Gln Arg Gln
             100                 105                 110

Gln Ser Arg Ala Lys Val Ser Ser Asn Val Cys Phe Thr Cys Asp Arg
         115                 120                 125

Ile Leu Gln Glu Pro Phe His Phe Cys Ser Leu Ser Cys Lys Val Asp
     130                 135                 140

Tyr Leu Ser Tyr Gln Gly Asp Asp Leu Ser Ser Ile Leu Tyr Arg Ile
145                 150                 155                 160

Asp Glu Ser Asp Phe Thr Phe Glu Gly Leu Arg Met Asp Gly His Asp
                 165                 170                 175

Gln Leu Gly Glu Ile Ser Thr Met Glu Asp Gly Glu Asp Ile Leu Val
             180                 185                 190

Ile Ser Asp Glu Ser Glu Gln Gly Asn Asn Ser His Lys Lys Glu Lys
         195                 200                 205
```

PROTEIN REGULATING LEAF LONGEVITY OF PLANTS, THE GENE THEREOF AND THEIR USE

TECHNICAL FIELD

The present invention relates to a protein responsible for the regulation of plant leaf longevity, a gene coding therefor, and uses thereof. More particularly, the present invention relates to a novel protein ORE15 capable of regulating plant leaf longevity, a novel gene ORE15 encoding the protein, and the use thereof for various purposes.

BACKGROUND ART

Plant senescence is a series of biochemical and physiological phenomena occurring in the last stage of the post-embryonic development of a plant, limiting the longevity of individual plants. The initiation of plant senescence is a turning point at which a drastic change occurs within cells, and the plants which are undergoing senescence decline in synthetic ability and have cellular structures and macro molecules degraded so as to lose cellular homeostasis, leading to cell death (Matile P. et al., Elservier, 413-440, 1992; Nooden L. D. et al., *Academic press*, 1988; Thiman K. V. et al., *CRC press*, 85-115, 1980; Thomas H. et al., *Annu. Rev. Plant Physiol.* 123:193-219, 1993). Plant senescence is not a simple passive degradation process of plant organs, but genetically programmed as a highly elaborated and active process that proceeds in cells, tissues, and organs.

In addition to biological importance, plant senescence is of industrial importance because it is relevant to the improvement of crop productivity and storability after harvest. Accordingly, genetic, molecular biological, physiological, and biochemical research has been actively conducted on plant senescence. However, most reports were obtained from research on plant hormones, and senescence regulation, such as the use of senescence regulating genes, has yet to be studied sufficiently.

Through reverse genetic methods, about 100 genes that increase in expression during leaf senescence have been found so far in mouse-ear cress, tomato, corn, rice, tobacco, and potato plants (Buchanan-Wallaston, *J. Exp. Bot.* 48: 181-199, 1997; Quirini et al., *Trends Plant Sci.* 5: 278-282, 2000). However, the functions of only a small number of the senescence-associated genes have been studied, with the properties of most remaining unknown. Recently, mutants that delay senescence have been isolated and studied in an attempt to find genes responsible for the regulation of leaf senescence (Woo H. R. et al., *Plant Cell* 13: 1779-1790, 2001; Woo H. R. et al., *Plant J.* (in press)). However, experimental difficulties have prevented senescence regulating genes from being isolated from senescence-promoting mutants.

DISCLOSURE

Technical Problem

It is an object of the present invention to provide a leaf longevity-regulating protein, named ORE15.

It is another object of the present invention to provide a plant leaf longevity-regulating gene, named ORE15, encoding the protein ORE15.

It is a further object of the present invention to provide a recombinant vector carrying the ORE15 gene.

It is still a further object of the present invention to provide a method for regulating plant longevity.

It is yet a further object of the present invention to provide a method for promoting the growth of a plant.

It is still another object of the present invention to provide a method for increasing biomass of plants.

It is yet another object of the present invention to provide a transgenic plant, exhibiting prolonged longevity.

It is yet still another object of the present invention to provide a transgenic plant, exhibiting growth enhancement.

It is yet still a further object of the present invention to provide a method for screening plant senescence-regulating genes.

It is an additional object of the present invention to provide a method for screening plant longevity regulation-associated material.

Technical Solution

In accordance with an aspect of the present invention, a protein, named ORE15, comprising the amino acid sequence of SEQ ID NO: 2 is found to have the function of regulating plant leaf longevity.

In accordance with another aspect of the present invention, a gene, named ORE15, encoding the leaf longevity-regulating protein ORE15 is provided.

In the present invention, genes associated with plant longevity are screened using *Arabidopsis thaliana*, which is a model plant for genetic and molecular biological study. Previously, the present inventors identified a senescence-associated gene, named ORE9 (Woo H. R. et al., *Plant Cell* 13:1779-1790, 2001). In the present invention, mutants of the factors responsible for senescence and novel senescence delay mutants, downstream of ORE9, are found. In this regard, a novel activation tagging method is applied to ore9-1, a senescence delay variant, to select mutants which show senescence delay more than does ore9-1. As a result, a novel gene was found to be associated with senescence and was named "ORE15".

The terms "longevity regulation" and "senescence regulation", as used herein, are synonymous with each other and may be interchangeably used without substantial difference. For example, life prolongation is substantially the same as senescence delay in plants. In this regard, the gene or protein of the present invention may be, in detail, described as a "life prolongation" or "senescence delay" gene or protein.

Also, it must be noted that the term "leaf longevity", as used herein in association with the gene or protein of the present invention, is adapted to more definitely express the target of the invention and must not be construed to limit the scope of the present invention. Although expressed as a leaf longevity-regulating gene or protein, the gene or protein of the present invention may be involved in the regulation of the longevity of other organs of a plant, such as roots, seeds, stems, flowers, and, further, in the regulation of the life span of the plant itself.

The plant leaf longevity-regulating protein ORE15 according to the present invention is (i) a polypeptide having an amino acid sequence 100% coincident with SEQ ID NO: 2. In consideration of the technology of the art, (ii) a polypeptide that contains a substantial part of the amino acid sequence of SEQ ID NO: 2, and (iii) a polypeptide substantially similar to that of (i) or (ii) are both sufficiently recognized to fall into the range of the plant leaf longevity-regulating protein ORE15.

As used herein, the term "a polypeptide that contains a substantial part of the amino acid sequence of SEQ ID NO: 2" means a polypeptide containing a part of the amino acid sequence of SEQ ID NO: 2, which still has the function of leaf longevity prolongation (that is, senescence delay) compared to the polypeptide consisting of the amino acid sequence of SEQ ID NO: 2, and retains a zinc finger motif. Because a senescence delay function and a zinc finger domain are sufficient for use in the present invention, the length and activity of the polypeptide are not important ("out of the question" means "permission denied"). Even if low in activity compared to the polypeptide containing the amino acid of SEQ ID NO: 2, any polypeptide that has the function of prolonging leaf longevity may be included within the range of "the peptide that contains a substantial part of the amino acid of SEQ ID NO: 2", irrespective of length.

Those skilled in the art, that is, those who understand the prior art related to the present invention, expect that a polypeptide containing the amino acid sequence of SEQ ID NO: 2, even if it is partially deleted, will still have the function of longevity prolongation. As such, there is a polypeptide that contains the amino acid sequence of SEQ ID NO: 2, with the deletion of an N- or C-terminal part. Generally, it is accepted in the art that even if its N- or C-terminal part is deleted, a mutant polypeptide retains the function of the intact polypeptide. In addition, a mutant polypeptide can still retain the function of the intact ORE 15 protein even if parts other than the N- or C-terminal part are deleted therefrom.

Accordingly, it must be understood in the present invention that a polypeptide containing a substantial part of the amino acid sequence of SEQ ID NO: 2 means any deletion mutant that can be prepared on the basis of the disclosure of the invention by those skilled in the art to retain both the function of leaf longevity prolongation and the zinc finger domain.

The phase "a polypeptide substantially similar to that of (i) or (ii)" means a mutant that has at least one substituted amino acid residue but still retains the physiological and structural functions of the amino acid sequence of SEQ ID NO: 2, that is, leaf longevity prolongation and a zinc finger domain. If a mutant in which at least one amino acid residue is substituted still shows the function of leaf longevity prolongation and retains a zinc finger domain, its activity or substitution percentage is not important. Accordingly, no matter how much lower a mutant polypeptide is in activity than a polypeptide containing the intact amino acid sequence of SEQ ID NO: 2, or no matter how abundant a mutant polypeptide is in substituted amino acid residues compared to a polypeptide containing the intact amino acid sequence of SEQ ID NO: 2, the mutant polypeptide is included within the scope of the present invention if it shows the function of leaf longevity prolongation and has a zinc finger domain.

Even though having at least one amino acid residue substituted for a corresponding residue of the intact polypeptide, a mutant polypeptide still retains the function of the intact polypeptide if the substituted amino acid residue is chemically equivalent to the corresponding one. For instance, when alanine, a hydrophobic amino acid, is substituted with a similarly hydrophobic amino acid, e.g., glycine, or with a more hydrophobic amino acid, e.g, valine, leucine or isoleucine, the polypeptide(s) containing such substituted amino acid residue(s) still retain(s) the function of the intact polypeptide, even if lower in activity. Likewise, a polypeptide containing substituted amino acid residue(s), resulting from substitution between negatively charged amino acids, e.g., glutamate and aspartate, still retains the function of the intact polypeptide, even if having lower activity. Also, this is true of a mutant polypeptide in which substitution occurs between positively charged amino acids. For example, a substitution mutant polypeptide, containing lysine instead of arginine, still shows the function of the intact polypeptide even if its activity is lower. In addition, polypeptides which contain substituted amino acid(s) in their N- or C-terminal parts still retain the function of the intact polypeptide.

Current technology in the art makes it possible to prepare a substitution mutant polypeptide that retains a zinc finger domain and shows the same function as in the intact polypeptide.

As described above, the "polypeptide substantially similar to that of (i) or (ii)" is understood to include all polypeptides that show the same longevity prolongation function as in the intact polypeptide in spite of the presence of at least one substituted amino acid therein, and retain zinc finger domains. Nevertheless, a polypeptide which shares higher homology with the amino acid sequence of SEQ ID NO: 2 is more preferable from the point of view of activity. Useful is a polypeptide that shows 60% or higher homology with the wild type polypeptide, with the best preference for 100% homology.

In more detail, more preferable are sequence homologies of 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%, in ascending order of preference.

In accordance with the present invention, the plant leaf longevity-regulating gene ORE15 includes polynucleotide sequences coding not only for the ORE15 protein of SEQ ID NO: 2, but also for its variants. In detail, not only a polynucleotide sequence encoding the ORE15 protein of SEQ ID NO: 2, but also any polynucleotide sequence encoding a protein that shows leaf longevity prolongation activity and has a zinc finger domain falls into the scope of the present invention. Most preferably, the ORE15 gene of the present invention includes a base sequence as listed in SEQ ID NO: 1.

In accordance with another embodiment of the present invention, a recombinant vector carrying the ORE15 gene is provided.

In a preferred example, the vector of the present invention contains (a) a nucleotide sequence encoding the protein ORE15, responsible for plant longevity prolongation, and (b) a promoter operably linked to the nucleotide sequence.

The term "operably linked", as used herein, means that a regulatory sequence (i.e., promoter, signal sequence or array of transcription factor binding sites) is functionally linked to another nucleotide sequence, thereby regulating the transcription and/or translation of this nucleotide sequence.

The vector system according to the present invention may be constructed by various methods well known in the art, which are described in detail by Sambrook et al., *Molecular Cloning, A Laboratory Manual*, Cold Spring Harbor Laboratory Press (2001), the disclosure of which is incorporated by reference herein.

Because it is isolated from plants and functions to prolong plant longevity, the gene of the present invention is the most applicable to plants. Accordingly, the present invention provides a plant expression vector comprising (i) a nucleotide sequence encoding the plant longevity prolongation protein ORE15; (ii) a promoter operably linked to the nucleotide sequence of (i), enabling a corresponding RNA molecule to be formed in plant cells; and (iii) a 3'-non-translation region causing polyadenylation at the 3'-terminus end of the RNA molecule in plant cells.

In a preferred example, the promoter useful in the present invention may be any one that is usually used in the art for the introduction of genes into plants. For example, a ubiquitin promoter obtained from corn, a cauliflower mosaic virus (CaMV) 35S promoter, a nopaline synthase (nos) promoter, a figwort mosaic virus 35S promoter, a sugarcane bacilliform virus promoter, a commelina yellow mottle virus promoter, a light-inducible promoter from the small subunit of ribulose-1,5-bis-phosphate carboxylase (ssRUBISCO), a rice cytosolic triosephosphate isomerase (TPI) promoter, an adenine phosphoribosyltransferase (APRT) promoter of *Arabidopsis thaliana*, and an octopine synthase promoter may be used in the present invention.

In a preferred example, the 3'-non-translation region causing the polyadenylation useful in the present invention may include a derivative from the nopaline synthase gene of *Acrobacterium tumefaciens* (nos 3' end) (Bevan et al., *Nucleic Acids Research*, 11(2):369-385 (1983)), a derivative from the octopine synthase gene of *Acrobacterium tumefaciens*, a 3'-end of the protease inhibitor I or II gene of tomato or potato, or a CaMV 35S terminator.

Optionally, the vector may further carry a gene encoding a reporter molecule (luciferase or β-glucuronidase). In addition, the vector of the present invention may contain, as a selection mark, an antibiotic (e.g., neomycin, carbenicillin, kanamycin, spectinomycin, hygromycin, etc.)-resistant gene (e.g., neomycin phosphotransferase (nptII), hygromycin phosphotransferase (hpt), etc.).

In accordance with a further embodiment, the present invention provides a method for regulating plant longevity, comprising the introduction of the ORE15 gene into a plant.

In accordance with still a further embodiment, the present invention provides a transgenic plant that exhibits prolonged longevity, with the ORE15 gene introduced thereinto.

In accordance with yet a further embodiment, the present invention provides a method for promoting the growth of a plant, comprising the introduction of the ORE15 gene into the plant.

In accordance with still another embodiment, the present invention provides a transgenic plant that exhibits growth enhancement, with the ORE15 gene introduced thereinto.

In accordance with yet another embodiment, the present invention provides a method for increasing the production amount of plants, comprising the introduction of the ORE15 gene into the plants.

Plants transformed with the gene of interest exhibit longevity prolongation or an increase in growth/production. The transformants carrying the ORE15 gene can be identified through various indicators signifying prolonged longevity (e.g., delayed decrease in chlorophyll content, delayed loss in photosynthetic capacity, expression of senescence-associated genes) or signifying growth increase (e.g., increased increment of leaf weight and size).

As used herein, the term "plant(s)" must be understood to include not only mature plant(s) but also plant cells, tissues, and seeds to be grown to mature plant(s).

Example of the plant(s) useful in the present invention include food crops, such as rice, wheat, barley, corn, beans, potato, red beans, oats, millet, etc., vegetable crops, such as *arabidopsis*, cabbages, melons, pumpkins, green onions, onions, carrots, etc., industrial crops, such as ginseng, tobacco, cotton, sesame, sugarcane, beets, *perilla*, peanuts, rape, etc., fruit trees, such as apple, pear, jujube, kiwi, grape, tangerine, persimmon, plum, apricot, banana, etc., flowers, such as roses, gladiolas, gerbera, carnations, lilies, tulips, etc., and fodder crops, such as ryegrass, red clover, orchard grass, alfalfa, tall fescue, perennial ryegrass, etc.

It should be noted that the phrase "increasing the production amount of plants" or "production increase" means an increase in plant biomass, including an increase in the weight and/or size of plant organs, such as leaves, stems, etc.

The introduction of an exogenous polynucleotide, i.e., the ORE15 gene, into plants may be achieved by a method well known in the art (*Methods of Enzymology*, Vol. 153, 1987, Wu and Grossman Ed, Academic Press; the disclosure of which is incorporated by reference herein). Plants may be transformed with a vector, such as a plasmid or virus, anchoring the exogenous polynucleotide thereto, using a mediator, such as *Agrobacterium* sp., (Chilton et al., 1977, *Cell* 11:263:271; the disclosure of which is incorporated by reference herein), or by introducing the exogenous polynucleotide directly into plant cells (Lorz et al., 1985, *Mol. Genet.* 199:178-182; the disclosure of which is incorporated by reference herein). For instance, electroporation, microparticle bombardment, or polyethylene glycol-mediated uptake may be used for introducing a vector containing no T-DNA regions.

Widely used is a plant transformation method in which *Agrobacterium tumefaciens* harboring an exogenous polynucleotide is transfected into plant cells or seeds (see: U.S. Pat. Nos. 5,004,863, 5,349,124 and 5,416,011). Those skilled in the art can culture and grow the transfected plant cells or seeds into mature organisms.

The creation of the transgenic plant is preferably achieved by inserting the ORE15 gene responsible for senescence delay into an expression vector containing a regulatory sequence to construct a recombinant expression vector and introducing the recombinant vector into a flower plant.

More preferably, the transgenic plant is created by inserting an ORE15 gene responsible for senescence delay into an expression vector harboring a regulatory nucleotide sequence to construct a recombinant expression vector, transforming an *Agrobacterium* sp. with the recombinant expression vector, and transfecting the transformed *Agrobacterium* sp. into a plant. More particularly, the transformed *Agrobacterium* sp. is transformed *Agrobacterium tumefaciens*.

The term "regulatory nucleotide sequence" must be understood to include all sequences that have influence on the expression of a gene of interest. Examples of the regulatory nucleotide sequence include leader sequences, enhancers, promoters, etc., with preference for promoters.

The selection of transgenic plants can be accomplished by exposing transfected cultures to a selecting agent (e.g., metabolic inhibitor, antibiotic, and herbicide). Transfected plant cells harboring a selectable marker gene can grow and proliferate in the presence of such selecting agents. Examples of the selectable marker applicable to the present invention include a hygromycin phosphotransferase gene, a glycophosphate resistant gene, and a neomycin phosphotransferase (nptII) system, but are not limited thereto.

Development or re-differentiation from plant protoplasm or various explants is well known in the art. Plant cells transfected with *Agrobacterium* sp. carrying exogenous genes can be developed or re-differentiated according to a method well known in the art (see: U.S. Pat. Nos. 5,004,863, 5,349,124 and 5,416,011).

In accordance with still yet another embodiment, the present invention provides a method for screening plant senescence-regulating genes, comprising (a) expressing or activating the ORE15 gene in a plant cell; and (b) detecting genes that show a change in expression in the plant cell.

The ORE15 gene of the present invention is found to have influence on the expression of senescence-associated genes in the present invention (see: Example 4). That is, mutant plants in which the ORE15 gene is activated or overexpressed allow senescence-inducing genes to be more actively expressed than in wild type plants.

Based on this finding, senescence-regulating genes can be screened by detecting genes that show a change in expression pattern when expressing or activating the ORE15 gene in plant cells.

The detection of genes that change their expression patterns is well known in the art. For example, genes changed in expression patterns can be screened by amplifying transcripts in the presence of arbitrary primers (see: U.S. Pat. No. 5,599, 672). In this case, RT-PCR products are compared between the mutant plant, in which the ORE15 gene is activated, and the control plant, in which the ORE15 gene is not activated.

In accordance with yet still a further embodiment, the present invention provides a method for screening a plant longevity regulation-associated material, comprising (a) treating a plant with a material of concern; and (b) analyzing the expression of the ORE15 gene in the plant.

Upon treatment with a material, an increase in the expression of the ORE15 gene indicates that the material is regarded as capable of plant longevity prolongation (senescence delay).

The expression of the ORE15 gene can be quantitatively and qualitatively analyzed in various techniques known in the art. Largely, the analysis can be conducted at a gene and a protein level. For gene level analysis, primers synthesized on the basis of the base sequence of the ORE15 gene, determined by the present invention, may be used in PCR or as probes in hybridization (for this, DNA microarrays are convenient). Alternatively, a Northern blotting technique (see: Peter B. Kaufma et al., *Molecular and Cellular Methods in Biology and Medicine*, 102-108, CRC press) is useful for gene level analysis. As for analysis at a protein level, it may be quantitatively or qualitatively achieved through immunoassays (e.g., radioimmunoassays, radioimmunoprecipitation assays, enzyme-linked immunosorbent assays (ELISA), dot blot assays, Western blot assays, inhibitory or competitive assays and sandwich assays) using an antibody against the protein encoded by the ORE15 gene (see: *Enzyme Immunoassay*, E. T. Maggio, ed., CRC Press, Boca Raton, Fla., 1980; and Gaastra, W., Enzyme-linked immunosorbent assay (ELISA), in *Methods in Molecular Biology*, Vol. 1, Walker, J. M. ed., Humana Press, NJ, 1984).

ADVANTAGEOUS EFFECTS

As described hereinbefore, the delayed senescence phenotype of the ore15-D mutant is attributed to the activation of the ORE15 gene. That is, the activation of the ORE15 gene can lead to the delay of plant senescence. Accordingly, the longevity of plants can be regulated by transforming plants with the ORE15 gene responsible for leaf longevity. Further, the ORE15 gene and its ORE15 protein can be useful for the study of the senescence mechanism and research into senescence-associated genes and senescence-regulating materials.

BRIEF DESCRIPTION OF DRAWINGS

FIGS. 1 to 3 show the comparison between senescence of the wild type (Col-O) and the longevity-prolonged mutant ore15-D of *Arabidopsis thaliana* over time (a), change in chlorophyll content (b), and change in photosynthesis activity (c), respectively.

□Col ■: ore15-D

Fv: maximum variable fluorescence

Fm: maximum yield of fluorescence

FIGS. 4 to 7 shows comparisons between senescence of the wild type (Col-O) and the longevity-prolonged mutant ore15-D of *Arabidopsis thaliana* after dark treatment over time (a), change in chlorophyll content (b), change in photosynthesis activity (c), and expression patterns of senescence-associated genes through Northern blotting analysis (d):

SEN1: Senescence-associated gene 1

SEN4: Senescence-associated gene 4

FIG. 8 shows the insertion of the activation tagging vector pSKI015 into the genome of the senescence mutant ore15-D in a schematic view, and results of a Northern blotting assay using the wild type (Col-O) and the ore15-D mutant in which the ORE15 gene is expressed.

E: enhancer

BAR: herbicide-resistant gene pBS: loci at which an *E. coli* replication origin and an ampicillin-resistant gene are located.

FIG. 9 is a predicted amino acid sequence of the ORE15 protein, corresponding to SEQ ID NO: 2

FIGS. 10 and 11 show changes of the wild type (Col-O) and the ore15-D mutant in fresh leaf weight and leaf area.

FIG. 12 is a photograph showing difference in leaf size among the wild type (Col-O), the ore15-D mutant and the knock-out mutant (ore12-2KO) of *Arabidopsis thaliana*.

FIG. 13 is a photograph showing the anatomy of longitudinal cross sections of leaves from the wild type (Col-O), the overexpression mutant ore15-D, and the knock-out mutant (ore12-2KO) of *Arabidopsis thaliana* (bar size corresponding to 100 μm).

FIG. 14 is a table in which average values of cell counts in a lengthwise direction and a widthwise direction in the first layer of the palisade parenchyma of the wild type (Col-O), the overexpression mutant ore15-D, and the knock-out mutant (ore12-2KO) of *Arabidopsis thaliana* are summarized (numerals of parentheses are SE).

BEST MODE FOR INVENTION

A better understanding of the present invention may be obtained through the following examples which are set forth to illustrate, but are not to be construed as the limit of the present invention.

Example 1

Selection of Senescence-Delayed Mutant from *Arabidopsis thaliana*

First, mutation was induced in *Arabidopsis thaliana*. For this, an activation tagging vector pSKI015 (Weigel et al., *Plant Physiology* 122:1003-1014, 2000) (granted from the Weigel lab, U.S.A.) that contained four CaMV 35S enhancements located near the right border of T-DNA, and a bar gene (phosphinothricin acetyltransferase gene) conferring Basta resistance was introduced into *Agrobacterium tumefacience* ABI strain (granted from the Amasino lab, U.S.A.) using an eletroporation method, followed by selection in a medium containing kanamycin and carbenicillin. Thereafter, the *Agrobacterium tumefacience* strain carrying the pSKI015 vector was transfected into the *Arabidopsis thaliana* senescence-delay mutant ore9-1 (Woo H. R. et al. *Plant Cell* 13:1779-1790, 2001) using a floral dip method (Clough et al., *Plant J.,* 16(6):735-743, 1998). Seeds of the transfected *Arabidopsis thaliana* were selected in the presence of Basta herbicide. In a greenhouse maintained at 23° C., 10,000 plants of T1 line were grown, and the etiolation according to the chlorophyll loss attributed to aging was observed with the naked eyes. A mutant line, which showed lower leaf eliolation progress than did ore9-1, was selected and named ore15-D.

FIG. 1 shows time-dependent patterns of leaf senescence in *Arabidopsis thaliana* Colombia wild-type (Col-O) and the mutant ore15-D. As apparent from FIG. 1, the mutant ore15-D of the present invention is found to undergo greatly delayed senescence compared to the wild type.

Example 2

Examination of Expression of Senescence Delay Mutant ore15-D

In order to examine senescence delay characteristics of the ore15-D mutant, the leaf chlorophyll content and photosynthesis activity of the mutant ore15-D and the wild type (Col-O) were compared.

2-1) Measurement of Chlorophyll Content

Leaves from each sample were boiled at 80° C. in 95% ethanol to extract chlorophyll. Chlorophyll content was determined by absorbance at 648 nm and 664 nm and expressed as percentages with regard to the fresh weight of leaf material (Vermon et al., *Anal. Chem.* 32:1142-1150, 1960).

In the wild type (Col-O), chlorophyll content was measured to be 50% at 28 DAE (days after emergence), as shown in FIG. 2, with chlorosis starting at 24 DAE. In contrast, the chlorophyll content of ore15-D was maintained at 100% to 28 DAE and at about 25% even until 36 DAE.

2-2) Photosynthetic Activity

Photosynthetic activity was measured using Oh's method (Oh S. A. et al., *Plant Mol. Biol.* 30: 939, 1996). To begin with, leaves at each DAE were placed for 15 min in darkness and measured for chlorophyll fluorescence using a plant efficiency analyzer (Hansatech Instruments, Morfolk, England). Taking advantage of chlorophyll fluorescence, photosynthesis activity was expressed as the photochemical efficiency of PS II (photosystem II), given by the ratio of maximum variable fluorescence (Fv) to maximum value of fluorescence (Fm) (Fv/Fm). The higher the value, the better the photosynthetic efficiency.

Photosynthesis activity also showed a change pattern similar to that of chlorophyll content. While photosynthesis activity started to drastically decrease after 24 DAE in the wild type (Col-O), ore15-D showed a slow declination of photosynthesis after 28 DAE (see FIG. 3).

Taken together, the data obtained above imply that the ore15-D mutant type exhibits a delayed senescence phenotype, compared to the wild type, due to the mutation of ORE15, and that the senescence delay results from delayed biochemical declination in chlorophyll content and photosynthetic activity.

Example 3

Change in ore15-D Mutant Leaf Longevity According to Dark Treatment

The leaf longevity of the ore15-D mutant was measured in terms of change in photosynthesis activity and chlorophyll content according to dark treatment, a senescence-accelerating factor.

Each of 24 leaves (12 DAE) from the wild type (Col-O) and the ore15-D mutant was floated on 3 mM 2-[N-morpholino]-ethanesulfonic acid (pH 5.8) (hereinafter referred to as 'MES buffer'). While being placed at 22° C. in a completely dark box, the leaves were individually assayed every other day for photosynthetic activity and chlorophyll content, as in Example 2. FIG. 4 is a photograph showing senescence progression with time in the leaves of the wild type (Col-O) and mutant type ore15-D of *Arabidopsis thaliana* after the dark treatment. As shown in the photograph, the variant ore15-D of the present invention was greatly delayed in senescence, compared to the wild type. In addition, five days after the dark treatment, as depicted in FIGS. 5 and 6, the chlorophyll content and the photosynthetic activity were measured to be as much as 99.5% and 99%, respectively, in the mutant ore15-D, while being greatly reduced to 75% and 74%, respectively, in the wild type (Col-O), compared to those before the dark treatment.

Example 4

Expression of Senescence-Associated Genes in ORE15 Mutant

To examine the effect of ORE15 on senescence-associated genes (SAGs), the time-dependent expression pattern of each SAG protein during dark treatment was analyzed using Northern blots. Samples were the total RNA isolated at 0, 2, 4, and 6 DAT. 10 µg of the prepared total RNA was loaded on each lane, and SEN1 (GenBank, accession No. NM 119743) and SEN4 (GenBank, accession No. NM 119173) genes were used as probes.

The Northern blotting results are given in FIG. 7. As seen in FIG. 7, Col-O definitely increased in the expression of the senescence-associated genes SEN1 and SEN4 at 8 DAT with the progress of senescence. During the same time period, however, the expression of the SAGs in the ore15-D mutant did not increase until 12 DAT. This fact indicates that ORE15 mutation influences leaf longevity at a molecular level as well as at a physiological level.

Example 5

ORE15 Gene Cloning and Base Sequencing

In order to search genes near T-DNA, activated by the enhancer, in the ore15-D mutant, a plasmid rescue method (Weigel et al., *Plant Physiology* 122:1003-1014, 2000) was used for gene isolation. In FIG. 8, there is a schematic view of a part of the ore15-D mutant genome with the activation tagging vector pSKI015 inserted thereinto. Genomic DNA was isolated from the ore15-D mutant (Dellaporta et al., *Plant Mol. Biol. Rep.* 1:19-21, 1983). Afterwards, 5 µg of the genomic DNA was digested with EcoRI, precipitated in ethanol, and dried. The DNA digests were self-ligated and introduced into *E. coli* DH5α, which was then grown in the presence of ampicillin to select transformants.

The *E. coli* which was transformed with a plasmid containing an *E. coli* replication origin, a selection marker, both present within T-DNA, and a 7.0 kb plant genomic DNA segment near the right border of T-DNA was grown to form colonies on a selection plate. After preparing plasmids from the colonies, the base sequence near the right border of T-DNA was determined. In this regard, an oligomer was synthesized on the basis of a base sequence downstream of the EcoRI site used for the plasmid rescue method, and was used for the base sequencing. With reference to an *Arabidopsis thaliana* genome database, the open reading frame nearest the enhancer was found on the basis of the base sequence determined. The protein expressed from the ORE15 gene consisted of 243 amino acids, as seen in SEQ ID NO: 2 of FIG. 9.

Northern blotting analysis was conducted, using the ORE15 gene as a probe. Total RNA was isolated from the wild type (Col-O) and the mutant ore15-D, using TRI-reagent (Sigma). 10 μg of the total RNA was loaded in each lane on 1.2% agarose/formaldehyde gel, separated, and transferred onto a nylon membrane. After washing the nylon membrane for 5 min with 2×SSC to remove agarose debris, the RNA was fixed onto the nylon membrane using UV light (254 nm, 0.18 J/Sq·cm2). The blots transferred onto the nylon membrane were subjected to pre-hybridization and hybridization according to Park's method (Park et al., *Plant Mol. Biol.* 26:1725-1735, 1994).

The results are shown in FIG. 8. Whereas no expression of the ORE15 gene was observed in the wild type (Col-O), the gene was found to be over-expressed in the ore15-D mutant.

Example 6

Introduction of ORE15 Gene into Wild Type (Col-O)

To examine whether the delayed senescence phenotype of the ore15-D mutant resulted from the activation of the ORE15 gene, a 2.5 kb DNA segment containing the ORE15 gene was introduced into the wild type (Col-O) to induce overexpression. To this end, first, full-length ORE15 cDNA was isolated using RT-PCR. A DNA segment containing the ORE15 gene therein was inserted into a pGEM-T Easy vector (Promega Corporation Madison, Wis. U.S.A.) and the recombinant vector was named pORE15/GTE. pORE15/GTE was double-digested with BglII and BstEII to excise an ORE15 gene segment which was subsequently inserted into pCAMBIA3301 (Caberra, Australia). With the resulting recombinant vector, named pORE15/3301, *Agrobacterium tumefacience* AGL1 strain was transformed. According to the floral dip method (Clough et al., *Plant J.*, 16(6):735-743, 1998), the transformed *Agrobacterium tumefacience* AGL1 strain, named pAT-ORE15, was transfected into the wild type (Col-O). The delayed senescence phenotype of the transgenic *Arabidopsis thaliana* was the proof that the ORE15 gene is responsible for the regulation of leaf longevity in *Arabidopsis thaliana*.

Example 7

Change in Leaf Weight and Size of the ore15-D Mutant in Development

A higher increase in the leaf weight and size of the ore15-D mutant than in that of the wild type, featuring, along with the prolonged leaf longevity, the present invention, was examined according to developmental time.

At four-day intervals starting from the DAE (days after emergence) of leaf blade, weights and sizes of the leaves from the wild type (Col-O) and the ore15-D mutant were measured. As for leaf size, it was determined from the scanning data of leaves, using software, Scion image (NIH, USA). Results are given in FIG. 10. The difference in leaf weight between the wild type and the ore15-D mutant was significant starting at 8 DAE, and increased thereafter. In addition, as shown in FIG. 11, the ore15-D mutant also surpassed the wild type (Col-O) in leaf size starting at 8 DAE.

These phenotypic differences were confirmed among the wild type (Col-O), the overexpression mutant ore15-D, and the knock-out mutant ore15-2KO at 12 DAE. ore15-D was observed to greatly increase in leaf size compared with the wild type (FIG. 12), and such size increase was found in almost all organs of ore15-D as well as the leaves. To examine by which factor such a change in organ size is induced, longitudinal cross sections of leaves were anatomically observed (FIG. 13) and the third rosette leaf was anatomically analyzed (FIG. 14). In palisade parenchyma, the ore15-D mutant had slightly smaller cell sizes, but a greater cell population than had the wild type. Meanwhile, the knock-out mutant ore15-2KO showed phenotypes directly opposite to those of the overexpression mutant ore15-D. Accordingly, the phenotypic characteristics in the leaf organ of ore15-D are thought attributable to an increase in the cell number of palisade parenchyma rather than in the cell size, suggesting that ORE15 plays an important role in delaying plant senescence by regulating the number of cells.

Although additional experiments are required to examine whether such a phenomenon is a factor having direct influence on or an indirect effect on senescence regulation, an increase in leaf size and weight can be applied to various crops, resulting in a great improvement in productivity.

The invention claimed is:

1. A leaf longevity-regulating protein, named ORE15, having a 95% or more sequence homology to the amino acid sequence of SEQ ID NO: 2.

2. A plant leaf longevity-regulating gene, named ORE15, encoding the protein ORE15 of claim 1.

3. The plant leaf longevity-regulating ORE15 gene according to 2, having the nucleotide sequence of SEQ ID NO: 1.

4. A recombinant vector carrying the ORE15 gene of claim 2.

5. A method for regulating plant longevity, comprising the introduction of the gene of claim 2 into a plant.

6. A transgenic plant, exhibiting prolonged longevity, having the gene of claim 2 introduced thereinto.

* * * * *